United States Patent [19]

Foker

[11] Patent Number: 4,719,201

[45] Date of Patent: Jan. 12, 1988

[54] METHOD FOR STIMULATING RECOVERY FROM ISCHEMIA

[75] Inventor: John E. Foker, Minneapolis, Minn.

[73] Assignee: Regents of the University of Minnesota, Minneapolis, Minn.

[21] Appl. No.: 826,857

[22] Filed: Feb. 6, 1986

Related U.S. Application Data

[63] Continuation-in-part of Ser. No. 699,037, Feb. 7, 1985, Pat. No. 4,605,644.

[51] Int. Cl.$^4$ ............................................. A61K 31/70
[52] U.S. Cl. ........................................................ 514/23
[58] Field of Search .......................................... 514/23

[56] References Cited

PUBLICATIONS

H. G. Zimmer, et al., *Pflugers Arch.*, 376, 223 (1978).
H. I. Seifart, et al., *Basic Res. Cardiol.*, 75, 57 (1980).
J. E. Foker, et al., *J. Thorac. Cardiovasc. Surg.*, 80, 506 (1980).
H. G. Zimmer, *Science*, 220, 81 (1983).
M. K. Pasque, et al., in *J. Thorac. Cardiovasc. Surg.*, 83, 390 (1982).
H. B. Ward, et al., Amer. College of Surgeons, 1983 Surgical Forum XXXIV at pages 264–265.
J. M. Kriett, et al., *Circ.*, 68, Supp. III, p. 389 (1983).
M. Mauser, et al., *Circ.* 68, Supp. III, p. 389 (1983).
J. Kriett, et al., *J. Amer. Coll. Cardiol.*, 3, 544 (1984).
H. G. Zimmer, et al., *Science*, 223, 714 (1984).
H. G. Zimmer, et al., *Prog. Clinc. Pharmacol.*, 3, 13 (1982).
H. G. Zimmer, et al., *Pflugers Arch.*, 389, R–7 (1981).

*Primary Examiner*—J. R. Brown
*Assistant Examiner*—Elli Peselel
*Attorney, Agent, or Firm*—Merchant, Gould, Smith, Edell, Welter & Schmidt

[57] ABSTRACT

The perfusion of ischemic tissue with dilute physiological salt solutions containing ribose reduces the period required for tissue function recovery and for the restoration of tissue ATP levels.

6 Claims, No Drawings

METHOD FOR STIMULATING RECOVERY FROM ISCHEMIA

CROSS-REFERENCE TO RELATED APPLICATION

This application is a continuation-in-part of U.S. application Ser. No. 699,037, filed Feb. 7, 1985, now U.S. Pat. No. 4,605,644.

BACKGROUND OF THE INVENTION

In general, organ function is dependent on an adequate supply of energy which is generated within the cell and can be converted into cellular work. Cellular metabolism generates adenosine triphosphate (ATP), a molecule which contains high energy bonds. It is the energy contained in the ATP molecule which is released to perform cellular functions. Consequently, the balance between the supply and the demand for ATP molecules will be an important factor in the cell's ability to function.

Oxygen is supplied to the cells by the blood and most cellular energy production is tightly coupled to oxygen. Whenever the blood flow to an organ is interrupted, a state of ischemia exists. During ischemia, cellular ATP will be consumed and usually cannot adequately be replenished in the absence of a supply of oxygen. Ischemia can exist for only a portion of an organ when the blockage of the blood supply to the organ is not total. In addition to total ischemia, or no blood flow, there are intermediate degrees of ischemia. Whenever the demand for ATP exceeds the cell's ability to produce it, cellular ATP levels will fall.

Significant ischemia occurs during most cases of open heart surgery, all episodes of coronary occlusion or heart attack, all cases of organ transplantation, certain procedures such as liver shunt operations and a variety of other situations in which either significant stress or a period of shock has compromised the functioning of one or more organs of the body. In all of these situations, cellular energy metabolism is impaired, and its restoration is critical to the recovery of organ function.

For example, much of the increased safety of heart surgery has come from improved surgical techniques which can be used when the heart is still and quiet. A quiet heart is usually produced by cooling and depriving it of its blood supply. In addition, a cardioplegic solution is frequently injected into the vessels of the heart to produce cardiac standstill and to reduce its energy demand. Although these techniques have allowed enormous progress to be made in cardiac surgery, there is still a price to be paid for this period of ischemia. The result is a period of depressed function (low cardiac output) following the operation which may or may not be tolerated by the patient. Moreover, even if it is reversed, there is evidence that scarring can occur and later failure can result. There is also an increasing emphasis on prompt reversal of the ischemia of the heart due to myocardial infarctions. The goal is to relieve the ischemia before permanent damage occurs. If the blood vessel can be unblocked by any one of a variety of methods, then the area of tissue relieved of ischemia would benefit greatly from methods to enhance its recovery. Failure of recovery from ischemia due to myocardial infarctions or to open heart surgery accounts for nearly 500,000 deaths per year in the United States.

Because of the importance of this problem, a great deal of investigation has been directed to elucidating the mechanisms responsible for the recovery of myocardial cells from ischemia. It has been found that the chemical precursors of ATP are broken down during ischemia and are not available to restore ATP levels when blood flow returns. During ischemia the cellular energy reservoir of ATP is utilized, initially producing adenosine diphosphate (ADP), and adenosine monophosphate (AMP). Further catabolism results in degradation of these products to adenosine (Ad), inosine (Ino) and hypoxanthine (Hx). With reperfusion of the organ, the recovery of ATP levels in the cell is limited because of loss of these ATP precursors. Much of the Ad, Ino and Hx have leaked out of the cells and the remaining compounds cannot easily regenerate ATP. Furthermore, endogenous synthesis of ATP precursors through the purine biosynthetic pathway, the major normal route of synthesis, proceeds slowly, is metabolically demanding, and thus limits ATP recovery.

After a period of myocardial ischemia under the conditions of clinical open heart surgery, ATP levels require about ten days to fully recover. Myocardial function has been determined to require a similar period for full return. The most sensitive aspect of myocardial function was found to be the relaxation rather than the countraction phase of the heartbeat. It is the relaxation phase, or diostole, that requires almost ten days to return to normal. When relaxation is incomplete, the heart does not fill satisfactorily and, therefore, less blood is ejected with each beat.

The theory that a reduction in the ATP recovery time could lead to improved cardiac function has lead to research aimed both at preventing the initial loss of ATP precursors from the cell and at methods for the resupply of the precursors employed in ATP biosynthesis.

Many investigators have attempted to show that specific precursors will block the fall in ATP levels or will augment ATP recovery. Adenosine, adenine, inosine, 5-amino-4-imidazolcarboxamide riboside and ribose are some of the ATP precursors that have been marginally useful in increasing ATP regeneration. Most studies were of short duration, e.g., 2 hours or less and none were longer than 24 hours. Consequently, only partial ATP recovery was found, and none accomplished the complete return of ATP levels once severe depression had been induced.

For example, H. G. Zimmer, in *Science*, 220, 81 (1983) reported a study in which ATP levels were shown to be maintained for 24 hours in rats which were treated with ribose after being given a toxic dose of isoproterenol and subjected to constriction of the abdominal aorta. The combined stresses of catecholamine stimulation and increased blood pressure on the heart resulted in lowered myocardial ATP levels. Zimmer's conclusion was that "the reductions in ATP and total adenine nucleotides were prevented" by this treatment. In this study the hearts were not subjected to ischemia and the ability of ribose to enhance recovery after an ATP fall had occurred was not tested.

Seifart et al. in Basic Res. Cardiol. 75, 57 (1980) studied isolated, electrically-driven guinea pig atria in which adenine and ribose were found to "inhibit the loss of cardiac adenine and pyridine nucleotides during anoxia." In this study the isolated atria were stabilized for an hour then subjected to nitrogen to cause 2 hours of anoxia, not ischemia. The addition of adenine and ribose after one hour of anoxia reduced the fall in ATP levels during anoxia. No investigation was made of the ability of adenine and ribose to restore fallen ATP levels.

Other studies have found that precursors which are relatively distant in terms of the enzymatic steps required to reform ATP appear to be less efficient in inducing ATP recovery, while other structurally closely related ATP precursors such as adenosine, can exhibit undesirable side-effects such as renal vasoconstriction.

Therefore, a need exists for a general method for the treatment of ischemic tissue which (a) rapidly restores normal cellular ATP levels and (b) maintains these levels for the time required for permanent tissue recovery from the effects of ischemia. Furthermore, a specific need exists for a method to improve the recovery of myocardial function after partial or total occlusion.

BRIEF DESCRIPTION OF THE INVENTION

The present invention provides a method for reducing the period of recovery of tissue function following ischemic insult by perfusion of the tissue with a solution comprising ribose. My commonly-assigned application Ser. No. 699,037, filed Feb. 7, 1985 discloses a method to restore and maintain the ATP levels of ischemic tissue by infusing the tissue with a solution containing both adenine and ribose. I have now discovered that ribose is the most important ATP precursor to provide, and surprisingly, is capable of enhancing and maintaining recovery to essentially the same extent as is the use of an adenine-ribose mixture. Therefore, the present method also shortens the period required for substantially complete recovery of ATP levels from about ten days to about 1-2 days. Furthermore, with respect to cardiac tissue, the return of heart diastolic function was found to closely parallel the return of ATP levels.

Thus, ribose is infused in an amount effective to both restore and maintain tissue ATP levels substantially equal to those present in the preischemic state. It was expected that once an amount of ribose effective to restore the ATP level had been infused, the level would be maintained by the tissue. Surprisingly, it was found that the effects of ischemia, and the accompanying net ATP catabolism are not immediately reversed by the restoration of ATP levels and tissue function. Thus, both ATP levels and cardiac function were observed to fall following premature cessation of the ribose infusion. Therefore, the present method also comprises continuing the infusion for the full duration of the ischemic effects, e.g., until the net catabolism of ATP has ceased and a secondary fall will not occur, rather than merely to the extent necessary to restore the tissue ATP levels.

Ribose infusion is a physiologically innocuous procedure. The only undesired effect is a tendency to lower blood glucose, a condition which is easily monitored and corrected. Therefore, the method of the present invention need not be limited to extreme situations such as those accompanying cardiac surgery, but can be extended to any situation in which hypoxia threatens tissue function.

DETAILED DESCRIPTION OF THE INVENTION

The present method comprises the perfusion of postischemic tissue such as myocardial tissue, with an adenine-free solution comprising ribose dissolved to the desired concentration in an aqueous vehicle suitable for tissue perfusion. Preferred vehicles are those solutions comprising amino acids, sugars such as dextrose, fructose and invert sugar, protein hydrolysates, sodium chloride, potassium chloride, calcium chloride, sodium lactate and mixtures thereof. Such commerically-available intravenous fluids, and methods for their infusion, are disclosed in *Remington's Pharmaceutical Sciences*, A. Osol, Ed., Mack Publishing Co. (16th ed.) at pages 1488-1497, the disclosure of which is incorporated by reference herein.

The infusion rate of the ribose solution, the infusion period, and the total dose delivered can be varied over a wide range and will be dependent on a number of variables, including (a) the type of tissue perfused, (b) the extent of the ischemia, (c) the physical characteristics and condition of the subject and (d) the mode of administration of the infusion solution. Since the target tissue will commonly be treated by infusion of the ribose solution into the subject's bloodstream, the rate of administration of the perfusion solution can be readily adjusted. Widely-employed techniqes, such as those employed for the infusion of IV solutions, can be utilized for introduction of the present solutions into the circulatory system, either by direct input into the circulatory system or via introduction into an extracorporeal stream of the blood. In the case of patients requiring immobilization of the heart, the present solutions can be infused intravenously or can be infused directly into a chamber of the heart at or near the time that blood reperfusion is begun. An atrial infusion technique is fully set forth in the Examples.

Dilute solutions of ribose in normal (0.9%) saline were found effective to decrease the ATP recovery time following myocardial ischemia in the canine model. For example, infusion of a normal saline solution which is 80 mM in ribose at a rate of about 1 ml/min for about 24.0 hours afforded an eight-fold decrease in the ATP recovery time. During this treatment period, about 17.0 g of ribose were introduced into the circulatory system; a total dose of about 550-700 mg ribose/kg of body weight. The appropriate dose for the optimal recovery of ATP levels and cardiac function in a given human subject can be readily established via empirical studies including known assays for ATP levels, cardiac function and the like.

The invention will be further described by reference to the following detailed examples.

Example I—Recovery of the Working Canine Heart Following Global Myocardial Ischemia A. Surgical Protocol Conditioned dogs weighing 25 to 30 kg were anesthetized intravenously with thiopental (Sodium Pentothal) (12.5 mg/kg) and ventilated with a Harvard respirator with supplemental oxygen provided to maintain a paO$_2$ of at least 100 mm Hg. Anesthesia was maintained with nitrous oxide and halothane. Temperatures were monitored continuously with an esophageal temperature probe (Electromedics, Englewood, CA). A right thoracotomy was performed through the fifth intercostal space and the aorta was cannulated through the internal mammary artery for arterial pressure monitoring and blood sampling. Blood pressures were measured with Statham P23Db strain gauges and recorded along the lead II ECG tracings on a Dynagraph eight-channel recorder (Beckman Instruments, Inc., Schiller Park, IL). Blood gases were measured with a Model 326 Blood Gas Analyzer (Instrumentation Laboratory, Inc., Lexington, MA). Hemoglobin was measured with a Hemoglobinometer (Coulter Electronics Inc., Hialeah, FL). All instruments were calibrated at the beginning, middle, and end of each experiment. Silicone rubber catheters were placed in the left atrial appendage for pressure monitoring, the right atrial appendage for saline solution or drug infusion, and the coronary sinus for blood withdrawal. Catheter positions were confirmed at the completion of each study.

After anticoagulation with heparin (250 U·kg$^{-1}$), the animals were placed on total cardiopulmonary bypass (CPB) at normothermia (37° C.) according to standard techniques. The arterial perfusion was retrograde from the left femoral artery and the venous drainage from the superior and inferior venae cavae was via the right atrium. The azygos vein was ligated. The left ventricle was vented through the apex. Model S100A bubble oxygenators (Shiley, Inc., Irving, CA) were used. Mean aortic pressure was maintained at 60 to 80 mm Hg by adjusting pump flow to approximately 10 ml·kg$^{-1}$. min with a Biotronics electromagnetic flow transducer in the arterial infusion line.

B. Experimental Protocol

After beginning CPB, the dogs were allowed to stabilize for about 5 to 10 minutes. Nearly simultaneous left ventricular transmural and septal biopsies were performed for measurement of adenine nucleotide levels. Global myocardial ischemia was then produced by cross-clamping the ascending aorta at normothermia (37° C.) with total arrest occuring within 5 to 7 minutes. The left ventricle was decompressed through the biopsy site. While the aorta was clamped, a silicone rubber catheter with a Teflon felt sewing ring was sutured into the right ventricular free wall. After a 20-minute ischemic period, transmural and septal biopsies were repeated and the aortic cross-clamp was removed. A d-(−)-ribose (80 mM) in saline (0.9%) or saline alone infusion (1 ml/min) was started at the beginning of reperfusion via the right atrial catheter. Defibrillation was accomplished with 5 to 10 W/sec of direct current after 20 minutes of reperfusion, and 10 minutes later the dogs were weaned from CPB and the heparin was reversed with protamine sulfate (50 to 100 mg). The dogs were supported for an additional 60 minutes off CPB, the biopsy cannula was brought through the lateral chest wall, and the chest incision was closed. During this time lactated Ringer's solution and/or whole blood was infused to maintain a left atrial pressure of 5 to 8 mm Hg and a hematocrit level of 30% to 40%.

The infusion of either ribose or saline solution into the right atrium was continued for 24 or more hours after the end of the ischemic period. Depending on the study performed, groups of animals were given the ribose infusion for 24, 48, 96, or 120 hours and were followed for a total of 168 hours. Repeat septal biopsies were performed at 4 hours and 1,2,3,5, and 7 days after ischemia. Biopsies were taken sequentially from the apex of the septum toward the base of the septum to avoid rebiopsy of the same area.

C. Nucleotide and Nucleoside Assays.

Biopsies for adenine nucleotides and nucleosides were frozen within 1 second in liquid nitrogen-cooled 2-methylbutane. Blood samples were centrifuged and the plasma was mixed with equal parts of 2M perchloric acid. The tissue was extraced within 24 hours in 7.1% perchloric acid, homogenized, and centrifuged at 1000 xg. The supernatant was neutralized (pH 7.2) with 2N KOH, 0.4M imidazole, 0.4M KCl for myocardial biopsies, and saturated KOH for blood samples, centrifuged to remove potassium perchlorate, and stored at −70° C. ATP, ADP, AMP were assayed by the methods set forth in *Methods of Enzymatic Analysis*, H. V. Bergmeyer, Ed., Academic Press (1974) at pages 1777-8 and 2126-29 respectively, the disclosure of which is incorporated by reference herein.

Purine nucleoside levels were determined by the method of H. K. Webster, et al., *J. Chromatography*, Vol. 209, 283-292 (1981), the disclosure of which is incorporated by reference herein.

D. Reagents, Calculations and Statistical Analyses

Reagents.

High-performance liquid chromatography grade methanol was purchased from Fischer & Porter Co., Warminster, PA. All other chemicals were purchased from Sigma Chemical Co., St. Louis, MO.

Statistics.

Differences between and within animal groups were evaluated by multivariate analysis (MANOVA) on the differences from baseline according to the method of S. Wallenstein, et al., in *Circ. Res.*, Vol. 47, 1-9 (1980), the disclosure of which is incorporated by reference herein. Biopsy technique was compared by linear regression analysis according to the method of least squares. Values represent mean ± SE.

E. Results and Interpretation of Data

1. Effects of Ribose on Post-Ischemic Recovery

ATP levels in myocardial tissue before, and for 48 hours after, 20 minutes of normotheremic global ischemia are presented in Table 1. Data represent the values measured in septal biopsies in 16 control and treated dogs.

TABLE I

| | ATP Levels (nmol · mg wet wt$^{-1}$) in Treated and Control Animals+ | |
|---|---|---|
| | ATP levels | |
| Time | NS (n = 7) | R (n = 9) |
| Preischemic | 5.06 ± 0.18 | 5.02 ± 0.22 |
| 20 Min | 2.54 ± 0.16* | 2.57 ± 0.29* |
| 4 Hr | 2.33 ± 0.19 | 3.04 ± 0.26 |
| 24 Hr | 2.58 ± 0.26 | 4.14 ± 0.35* |
| 48 Hr | 2.70 ± 0.34 | 4.43 ± 0.32 |

Legend: NS = Normal saline controls; R = ribose.
+Values are mean ± SEM; p value is for treated versus control animals
(*p < 0.05 versus previous time point).

The data summarized in Table I demonstrate that ATP levels decreased about 50% at the end of ischemia in both groups. Within 4 hours the recovery of ATP in ribose-treated animals was already in evidence, while the ATP levels in the control animals were even lower than at the end of ischemia. The latter finding indicates that without treatment ATP levels continue to fall for a time despite reperfusion.

The recovery rate for ATP levels during the first 24 hours after ischemia in control animals was 0.3 nmol/mg wet weight/day and the projected complete recovery time was 9.9 days. In treated dogs, the mean recovery rate for ATP levels was 2 nmol/mg wet wt./day and the projected complete recovery time was 1.2 days (p<0.001; treated versus controls). Thus, regeneration of ATP could be enhanced about sevenfold with the ribose infusion, thus decreasing ATP recovery time from about 10 days to just over 24 hours.

The faster rate of ATP recovery in treated animals during the first 4 hours of precursor infusion suggests that regeneration of ATP levels is not linear with time, and that nearly complete recovery actually occurs even sooner than 24 hours.

The results indicate that ATP return can be greatly enhanced despite the demand of work on the recovering myocardium. ATP levels continued to decline during the first 4 hours of reperfusion in control dogs indicating that either the consequences of ischemia continue to produce net AMP breakdown (i.e., enzymatic degradation of AMP precursors continues at an increased rate) or the demands of cardiac function exceed the production of ATP.

2. Duration of Ribose-Dependent Post-Ischemic Recovery

The purpose of this study was to determine the required duration of ribose infusion following severe ischemia (Isc). Dogs were subjected to 20 minutes of normothermic global ischemia on cardiopulmonary bypass according to the procedure of Example I. Following ischemia, a group of six dogs received 1 ml/min infusion of 80 mM ribose in normal saline into the right atrium for 24 hr (R24), 48 hr (R48), 96 hr (R96) or 120 hr (R120). A control group of eight dogs (C) received normal saline (NS) at 1 ml/min into the right atrium. Left ventricular biopsies were taken pre-ischemia, at the end of ischemia, 4 hr after ischemia and daily thereafter. The biopsies were analyzed for adenine nucleotide content. The measured ATP levels are represented in Table II.

TABLE II

| | ATP Levels (umol/gm wet wt)+ | | | | | |
|---|---|---|---|---|---|---|
| | | | Post-Isc Period | | | |
| Infusion | C | 20 min. Isc/ | 24 hr | 48 hr | 72 hr | 120 hr |
| NS(48) | 5.26 ± 0.18 | 2.54 ± 0.16* | 2.58 ± 0.26 | 2.70 ± 0.34 | 3.39 ± 0.31 | 4.21 ± 0.47 |
| R(24) | 4.94 ± 0.22 | 2.57 ± 0.37* | 4.14 ± 0.24* | 3.95 ± 0.34 | 3.23 ± 0.52 | — |
| R(48) | 5.02 ± 0.22 | 2.57 ± 0.29* | 4.14 ± 0.35* | 4.43 ± 0.32 | 3.31 ± 0.33* | — |
| R(96) | 5.14 ± 0.31 | 1.78 ± 0.17* | 3.98 ± 0.07* | 4.58 ± 0.23 | 4.32 ± 0.31 | 3.65 ± 0.15 |
| R(120) | 5.20 ± 0.32 | 2.36 ± 0.43* | 4.62 ± 0.21* | 4.41 ± 0.27 | 4.40 ± 0.38 | 4.58 ± 0.20 |

+Mean ± SEM (*$p < 0.05$) in Treated and Control Animals.

The data summarized in Table II confirm that enhanced recovery of ATP following ischemia occurs with ribose infusions. In addition, these results reveal an unexpected requirement with respect to the total infusion time. Despite nearly complete recovery after 24 hours of ribose infusion, ATP levels again fell after cessation of ribose. Similar results were obtained when ribose was discontinued after 48 hours; thereafter ATP levels also fell to NS control levels. Continuing the ribose infusion for 96 hours, and thereafter stopping the infusion resulted in a subsequent fall. Only if the ribose infusion was continued for 120 hours was no secondary fall observed. These results indicate that although ATP recovery following ischemia can be greatly enhanced with a ribose infusion, the consequences of ischemia persist with continued net ATP catabolism, despite the fact that the recovery of ATP levels has been enhanced. Consequently, ATP precursor infusion must be continued for about 5 days, in order to maintain continued tissue energy recovery and, thereby, preventing the possibility of potentially serious deterioration of myocardial function.

The model systems presented in Examples IE(1) and IE(2) are designed to test the response of the intact, working heart to a moderate global ischemic insult, a situation resembling a majority of cardiac operations. Thus, tissue perfusion according to the present invention may also be considered as an appropriate metabolic intervention in the human clinical situation. For example, in addition to the need to immediately reverse the energetic depletion due to ischmia produced during heart surgery, it is becoming a routine in the post-surgical period to place patients whose hearts cannot maintain adequate systemic circulation on circulatory assistance for several hours or days. The above data suggest that a supplemental ribose infusion during these situations would also hasten the myocardial energetic recovery, thereby inproving survival and shortening the period of circulatory assistance.

Although the studies of the Examples were directed at enhancing the energetic recovery following ischemia of the heart, the present method is expected to be applicable to any tissue or organ that has suffered an ischemic insult, where reperfusion is possible. These situations include but are not limited to: myocardial infarction, stroke, organ transplant with organ preservation, neonatal support, multi-organ system failures, shock and trauma resulting in compromised circulation, and the like. Often, even uncomplicated general anesthesia can result in some degree of hypoxia. Therefore, the present invention provides a method whereby ischemic tissue can be treated so as to quickly regain and maintain normal ATP levels, both to improve tissue survival and to hasten general bodily recovery.

The invention has been described with respect to various specific and preferred embodiments. However, it should be understood that many variations or modifications may be made while remaining within the spirit and scope of invention.

What is claimed is:

1. A method for reducing the recovery time of tissue function following ischemic insult comprising:
    (a) perfusing said tissue with an adenine-free solution incorporating ribose for about 24 hours in an amount effective to restore the tissue ATP level and tissue function to levels substantially equal to those present in the preischemic tissue; and
    (b) continuing said perfusion until the tissue maintains its restored function and ATP level when the perfusion is discontinued.

2. The method of claim 1 wherein said tissue is myocardial tissue.

3. The method of claim 2 wherein said ischemic insult is due to a myocardial infarction.

4. The method of claim 3 wherein said ischemic insult is produced during heart surgery.

5. The method of claim 3 wherein the ribose solution is infused directly into a chamber of the heart or is infused intraveneously.

6. The method of claim 2 wherein a solution of ribose in an intravenous solution is perfused.

* * * * *

UNITED STATES PATENT AND TRADEMARK OFFICE
CERTIFICATE OF CORRECTION

PATENT NO. : 4,719,201

DATED : January 12, 1988

INVENTOR(S) : John E. Foker

It is certified that error appears in the above-identified patent and that said Letters Patent is hereby corrected as shown below:

Col. 1, after the Title, please add the following paragraph:

"This invention was made with government support under HL 26640 and HL 22152 awarded by the National Institutes of Health. The government has certain rights in the invention."

Signed and Sealed this

First Day of July, 1997

Attest:

BRUCE LEHMAN

*Attesting Officer*   *Commissioner of Patents and Trademarks*